United States Patent
Ehman et al.

(10) Patent No.: US 7,307,423 B2
(45) Date of Patent: Dec. 11, 2007

(54) MAGNETIC RESONANCE ELASTOGRAPHY USING MULTIPLE DRIVERS

(75) Inventors: Richard L. Ehman, Rochester, MN (US); Phillip J. Rossman, Rochester, MN (US)

(73) Assignee: Wisconsin A.umni Research Foundation, Madison, WI (US)

( * ) Notice: Subject to any disclaimer, the term of this patent is extended or adjusted under 35 U.S.C. 154(b) by 163 days.

(21) Appl. No.: 11/122,424

(22) Filed: May 5, 2005

(65) Prior Publication Data
US 2006/0253020 A1 Nov. 9, 2006

(51) Int. Cl.
*G01V 3/00* (2006.01)
*A61B 8/14* (2006.01)

(52) U.S. Cl. ..................... 324/318; 600/459

(58) Field of Classification Search ........ 324/300–322; 600/407–435, 481–528
See application file for complete search history.

(56) References Cited

U.S. PATENT DOCUMENTS

| | | | |
|---|---|---|---|
| 5,451,876 A * | 9/1995 | Sandford et al. ........... 324/322 |
| 5,592,085 A * | 1/1997 | Ehman ..................... 324/309 |
| 5,606,971 A | 3/1997 | Sarvazyan |
| 5,810,731 A | 9/1998 | Sarvazyan et al. |
| 5,952,828 A | 9/1999 | Rossman et al. |
| 5,977,770 A | 11/1999 | Ehman |
| 6,025,718 A * | 2/2000 | Hushek ..................... 324/316 |
| 6,037,774 A | 3/2000 | Felmlee et al. |
| 6,097,977 A * | 8/2000 | Collick et al. ............. 600/410 |
| 6,486,669 B1 | 11/2002 | Sinkus et al. |
| 6,862,468 B2 * | 3/2005 | Smith ....................... 600/410 |
| 6,879,155 B2 * | 4/2005 | Ehman et al. ............. 324/309 |
| 6,937,883 B2 * | 8/2005 | Prince ....................... 600/411 |
| 7,041,058 B2 * | 5/2006 | Piehler ..................... 600/437 |
| 2006/0264736 A1 * | 11/2006 | Ehman et al. ............. 600/410 |

* cited by examiner

*Primary Examiner*—Brij Shrivastav
*Assistant Examiner*—Dixomara Vargas
(74) *Attorney, Agent, or Firm*—Quarles & Brady LLP

(57) ABSTRACT

A magnetic resonance elastography (MRE) scan is performed using an array of transducers for applying a strain wave to tissues in a region of interest. A calibration process is performed prior to the scan in which the strain wave produced by each transducer in the array is imaged using an MRE pulse sequence so that information may be acquired that enables each transducer to be properly driven during a subsequent MRE scan.

8 Claims, 5 Drawing Sheets

MAGNETIC RESONANCE ELASTOGRAPHY USING MULTIPLE DRIVERS

STATEMENT REGARDING FEDERALLY SPONSORED RESEARCH

This invention was made with government support under Grant Nos. EB001981 and CA91959 awarded by the National Institute of Health. The United States Government has certain rights in this invention.

BACKGROUND OF THE INVENTION

The field of the invention is magnetic resonance imaging (MRI) methods and systems. More particularly, the invention relates to devices for implementing MR elastography.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (e.g. of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the NMR signals, and from this the mechanical properties of the subject can be determined. In many applications, the production of shear waves in the tissues is merely a matter of physically vibrating the surface of the subject with an electromechanical device such as that disclosed in above-cited U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver devices have been developed to produce the oscillatory force needed to practice MRE. As disclosed in U.S. Pat. Nos. 5,977,770; 5,952,828; 6,037,774 and 6,486,669 these typically include a coil of wire through which an oscillating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver as described in co-pending U.S. patent application Ser. No. 10/860,174 filed on Jun. 3, 2004 and entitled "Pressure Activated Driver For Magnetic Resonance Elastography". The acoustic driver is located remotely from the MRI system and is acoustically coupled by a tube to a passive actuator positioned on the subject being imaged. The passive activator does not disturb the magnetic fields and it may be oriented in any direction.

Regardless of the type of MRE driver used, there are clinical situations where a single MRE driver cannot be positioned to adequately vibrate, or illuminate, tissues in the region of interest. In some situations the vibrations are unevenly attenuated, or in some situations the region of interest is in the shadow of a structure that attenuates the vibrations.

SUMMARY OF THE INVENTION

The present invention employs a phased-array of MRE drivers to produce vibration of tissues in a region of interest. Each MRE driver applies an independently-controlled oscillatory stress to the subject, and in a prescan process the waveform separately produced by each MRE driver is imaged using an MRE pulse sequence. The magnitude and phase of the prescan waveform produced by each separate MRE driver is used to determine how the MRE driver should be driven so that the total illumination of the region of interest is optimal during an MRE scan.

A general object of the invention is to provide more uniform illumination of tissues in a region of interest. The separate MRE drivers may be positioned around the region of interest and the oscillatory strain wave produced in the region of interest by each MRE driver may be measured and adjusted during the prescan such that the cumulative strain wave produced by the MRE driver array is optimal.

DETAILED DESCRIPTION OF THE PREFERRED EMBODIMENT

Figure 1:
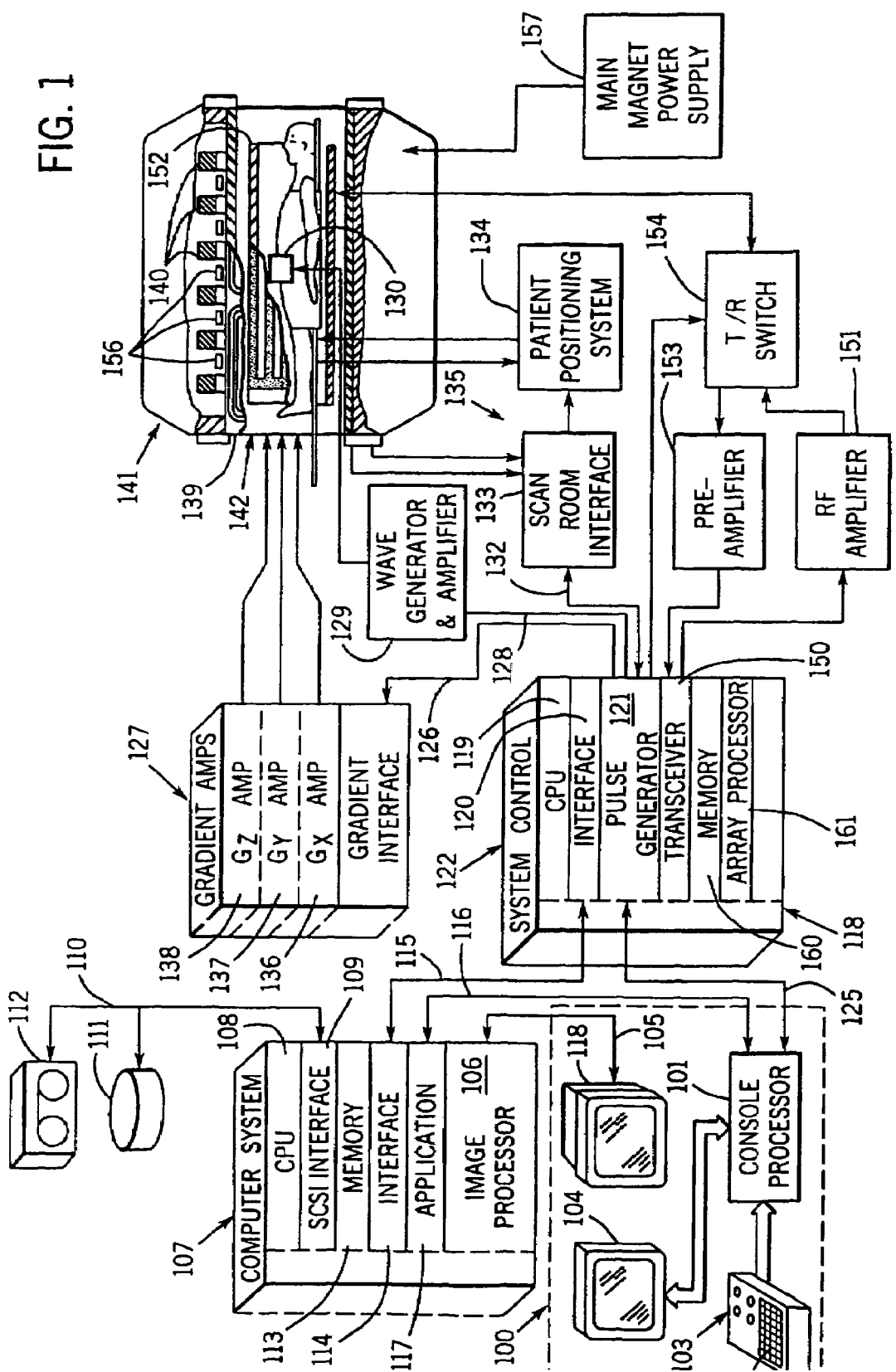
FIG. 1 is a block diagram of an MRI system which has been modified to practice a preferred embodiment of the invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 includes a number of modules which communicate with each other through a backplane. In addition to the application interface 117 and the image processor 106, these include a CPU module 108 that controls the backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan.

In the preferred embodiment of the invention the pulse generator module 121 also produces sync pulses through a serial link 128 to wave generator and amplifier assembly 129. The wave generator produces sinusoidal voltages which are output to dc coupled audio amplifiers as will be described in more detail below. A frequency in the range of 20 Hz to 1000 Hz is typically produced depending on the particular object being imaged, and one or more transducers in an array 130 are driven by these signals as will be described in more detail below. The transducer array 130 produces a force, or pressure, which oscillates and creates an oscillating stress in the gyromagnetic media (i.e. tissues) to which it is applied.

And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$, and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 141 which includes a polarizing magnet 140 that produces either a 0.5 or a 1.5 Tesla polarizing field that extends horizontally through a bore 142. The gradient coils 139 encircle the bore 142, and when energized, they generate magnetic fields in the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_0$, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_0 + G_x x + G_y y + G_z z$. The gradient magnetic fields are utilized to encode spatial information into the NMR signals emanating from the patient being scanned, and as will be described in detail below, they are employed to measure the microscopic movement of spins caused by the pressure produced by the transducer array 130.

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil 152 are digitized by the transceiver module 150 and transferred to a memory module 160 which is also part of the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 as will be described in more detail below and conveyed to the operator console 100 and presented on the video display 118.

Figure 2:
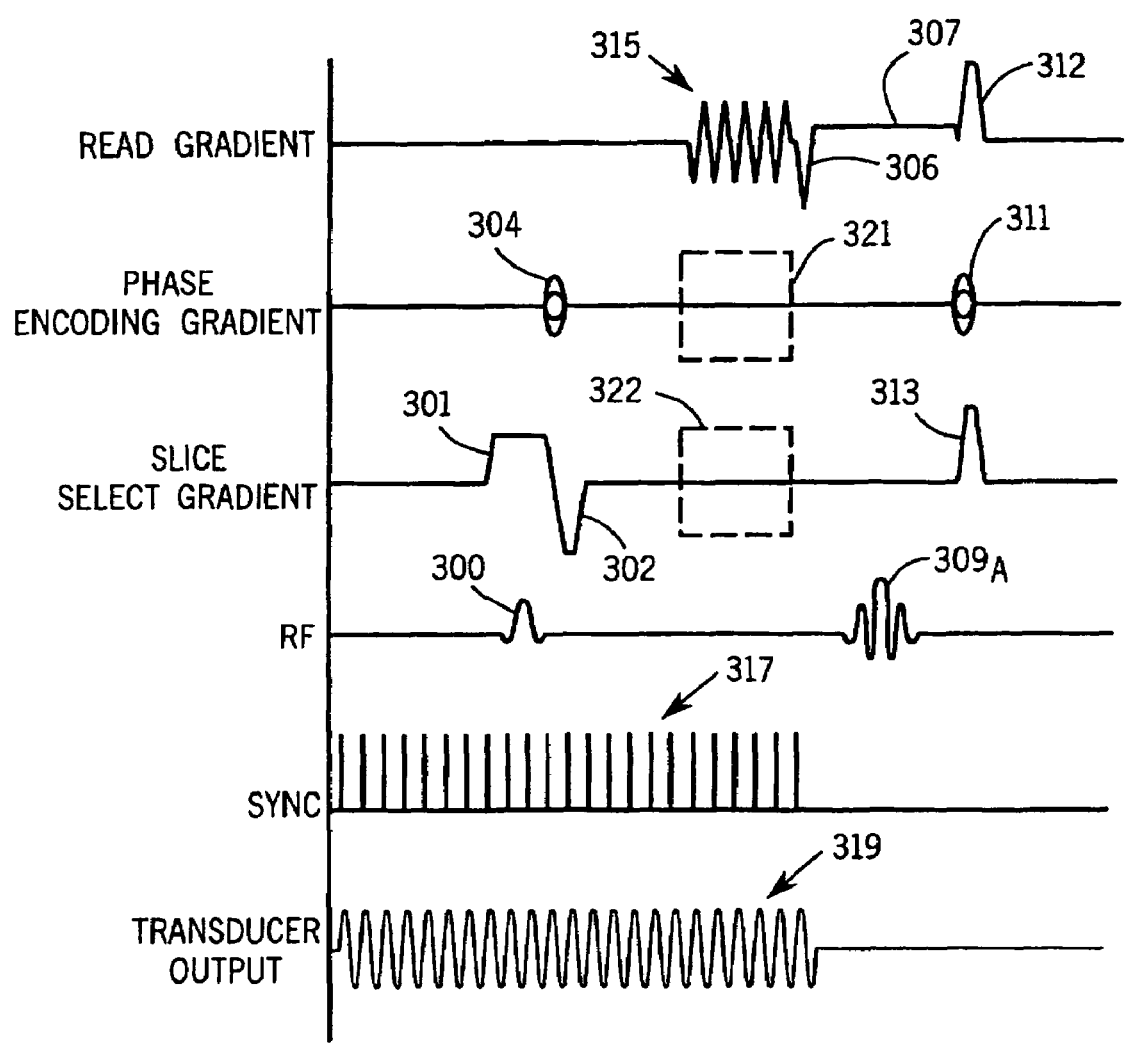
FIG. 2 is a graphic representation of a preferred MRE pulse sequence employed by the MRI system of FIG. 1.

Referring particularly to FIG. 2, a preferred embodiment of a pulse sequence which may be used to acquire NMR data according to the present invention is shown. The pulse sequence is fundamentally a 2DFT pulse sequence using a gradient recalled echo. Transverse magnetization is produced by a selective 90° rf excitation pulse 300 which is produced in the presence of a slice select gradient ($G_z$) pulse 301 and followed by a rephasing gradient pulse 302. A phase encoding gradient ($G_y$) pulse 304 is then applied at an amplitude and polarity determined by the view number of the acquisition. A read gradient ($G_x$) is applied as a negative dephasing lobe 306, followed by a positive readout gradient pulse 307. An NMR echo signal 309 is acquired 40 msecs. after the rf excitation pulse 300 during the readout pulse 307 to frequency encode the 256 digitized samples. The pulse sequence is concluded with spoiler gradient pulses 312 and 313 along read and slice select axes, and a rephasing gradient pulse 311 is applied along the phase encoding axis ($G_y$). As is well known in the art, this rephasing pulse 311 has the same size and shape, but opposite polarity of the phase encoding pulse 304. The pulse sequence is repeated 128 times with the phase encoding pulse 304 stepped through its successive values to acquire a 128 by 256 array of complex NMR signal samples that comprise the data set (A).

An alternating magnetic field gradient is applied after the transverse magnetization is produced and before the NMR signal is acquired. In the preferred embodiment illustrated in FIG. 2, the read gradient ($G_x$) is used for this function and is alternated in polarity to produce bipolar, gradient waveforms 315. The frequency of the alternating gradient 315 is set to the same frequency used to drive the transducers in the array 130, and it typically has a duration of 25 msecs. At the same time, the pulse generator module 121 produces sync pulses as shown at 317, which have the same frequency as and have a specific phase relationship with respect to the alternating gradient pulses 315. These sync pulses 317 are used to produce the drive signals for the MRE transducer array 130 to apply an oscillating stress 319 to the patient. To insure that the resulting waves have time to propagate throughout the field of view, the sync pulses 317 may be turned on well before the pulse sequence begins, as shown in FIG. 2.

The phase of the NMR signal 309 is indicative of the movement of the spins. If the spins are stationary, the phase of the NMR signal is not altered by the alternating gradient pulses 315, whereas spins moving along the read gradient axis (x) will accumulate a phase proportional to their velocity. Spins which move in synchronism and in phase with the alternating magnetic field gradient 215 will accumulate maximum phase of one polarity, and those which move in synchronism, but 180° out of phase with the alternating magnetic field gradient 215 will accumulate maximum phase of the opposite polarity. The phase of the acquired NMR signal 309 is thus affected by the "synchronous" movement of spins along the x-axis.

The pulse sequence in FIG. 2 can be modified to measure synchronous spin movement along the other gradient axes (y and z). For example, the alternating magnetic field gradient pulses may be applied along the phase encoding axis (y) as indicated by dashed lines 321, or they may be applied along the slice select axis (z) as indicated by dashed lines 322. Indeed, they may be applied simultaneously to two or three of the gradient field directions to "read" synchronous spin movements along any desired direction.

The present invention may be implemented using most types of MR imaging pulse sequences. Gradient echo sequences can be readily modified to incorporate the alternating gradient as illustrated in the preferred embodiment. In some cases, however, the characteristics of a gradient echo sequence may not be ideal for a particular application of the technique. For example, some tissues (such as those with many interfaces between materials with dissimilar magnetic susceptibilities) may have a relatively short T2* relaxation time and therefore may not provide enough signal to obtain a noise-free image at the required echo delay placement of the separate drivers 130a and 130b on the subject. Consequently, it is necessary to determine what these settings should be prior to each MRE scan.

Figure 4:
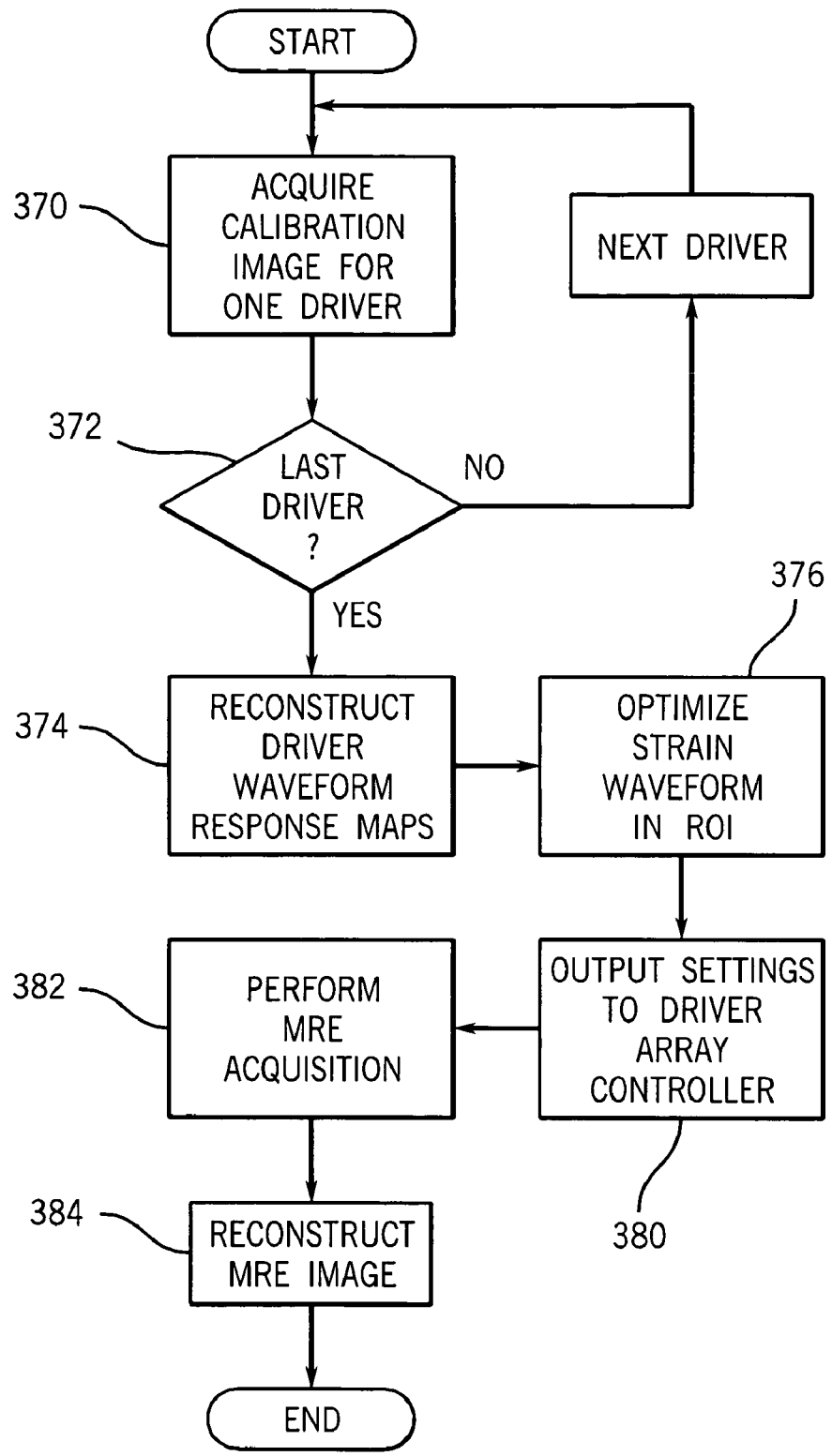
FIG. 4 is a flow chart of the steps performed by the MRI system of FIG. 1 when practicing a preferred embodiment of the present invention.

Referring particularly to FIG. 4, when an MRE scan is to be performed with the transducer array 130, each driver is first separately driven in a calibration acquisition as indicated by process block 370. This calibration acquisition employs an MRE pulse sequence such as that described above with reference to FIG. 2. As will be described below in more detail, several images are acquired for each separate driver in the array 130 in which the phase of the driver signal (as determined by the sync pulses 317) is set to different values relative to the phase of the motion encoding gradient 315. After all the drivers have been separately operated as determined at decision block 372, driver waveform response maps are reconstructed as indicated at process block 374. As a result of this calibration image acquisition step, settings are downloaded to the driver array controller 360 for each driver. Exemplary settings are as follows.

| Transducer 130a | |
|---|---|
| Frequency | 100 Hz |
| Amplitude | 10 volts |
| Relative Phase | 0 degrees |
| Transducer 130b | |
| Frequency | 100 Hz |
| Amplitude | 15 volts |
| Relative Phase | 180 degrees |

Figure 5:
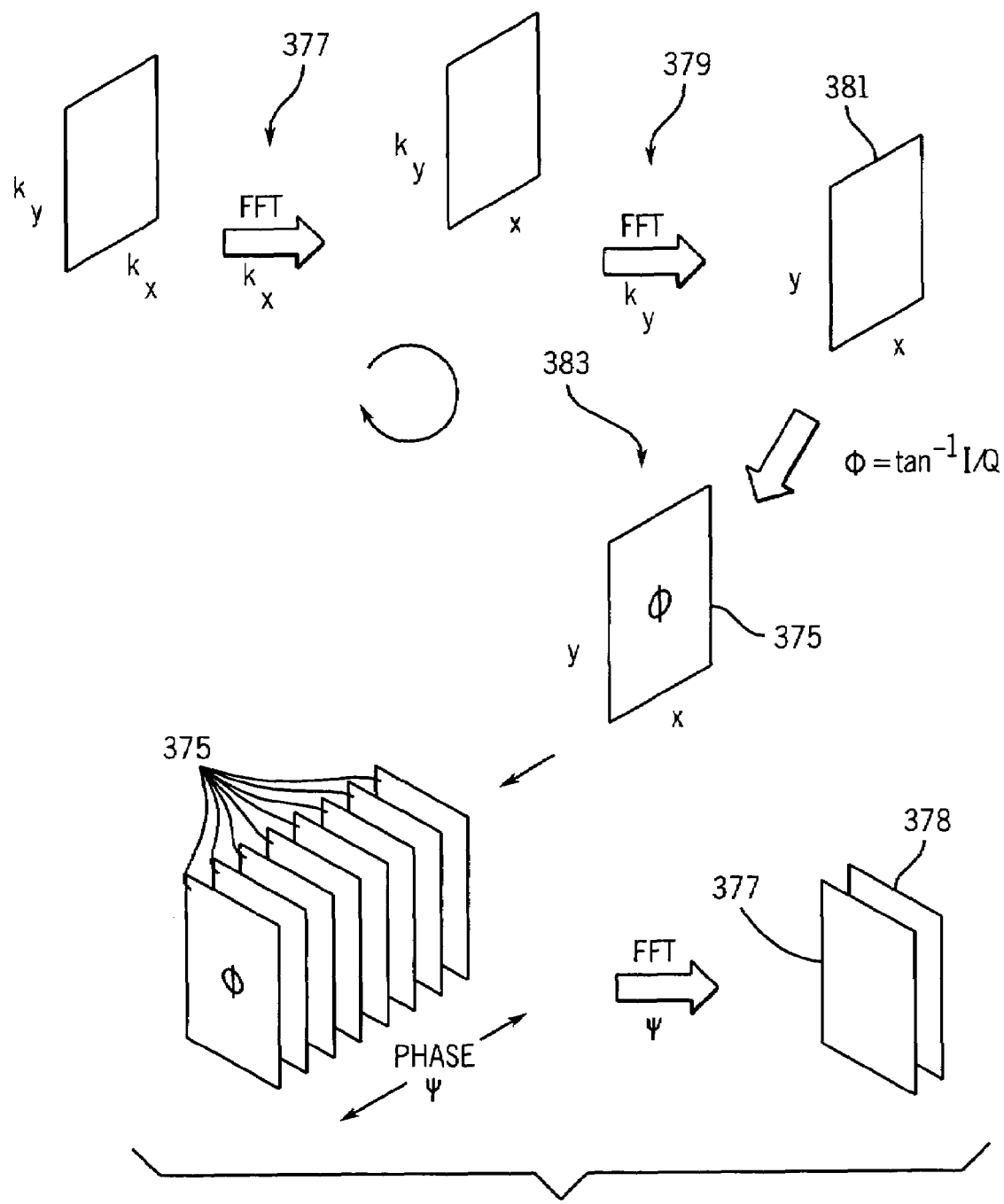
FIG. 5 is a pictorial representation of data structures produced when practicing the method of FIG. 4.

The driver waveform response maps are produced using the method disclosed in U.S. Pat. No. 5,592,085 which is incorporated herein by reference. Referring particularly to FIG. 5, the acquired MRE data is first Fourier transformed along the readout gradient axis as indicated at 377 and then Fourier transformed along each of the one or more phase encoding gradient axes as indicated at 379. These are complex Fourier transformations and the resulting image 381 has complex values I and Q at each image pixel. The phase at each resulting image pixel is then calculated ($\phi\tan^{-1}$ I/Q) as indicated at 383 to produce a phase image time. In this setting, a spin echo implementation of the invention may be ideal, because for a given echo delay time TE, this pulse sequence is much less sensitive to susceptibility effects than a gradient echo sequence. When a spin echo pulse sequence is used, the alternating magnetic field gradient can be applied either before and/or after the 180° rf inversion pulse. However, if the alternating gradient is applied both before and after the rf inversion pulse, the phase of the alternating magnetic field gradient must be inverted 180° after the rf inversion pulse in order to properly accumulate phase.

Figure 3:
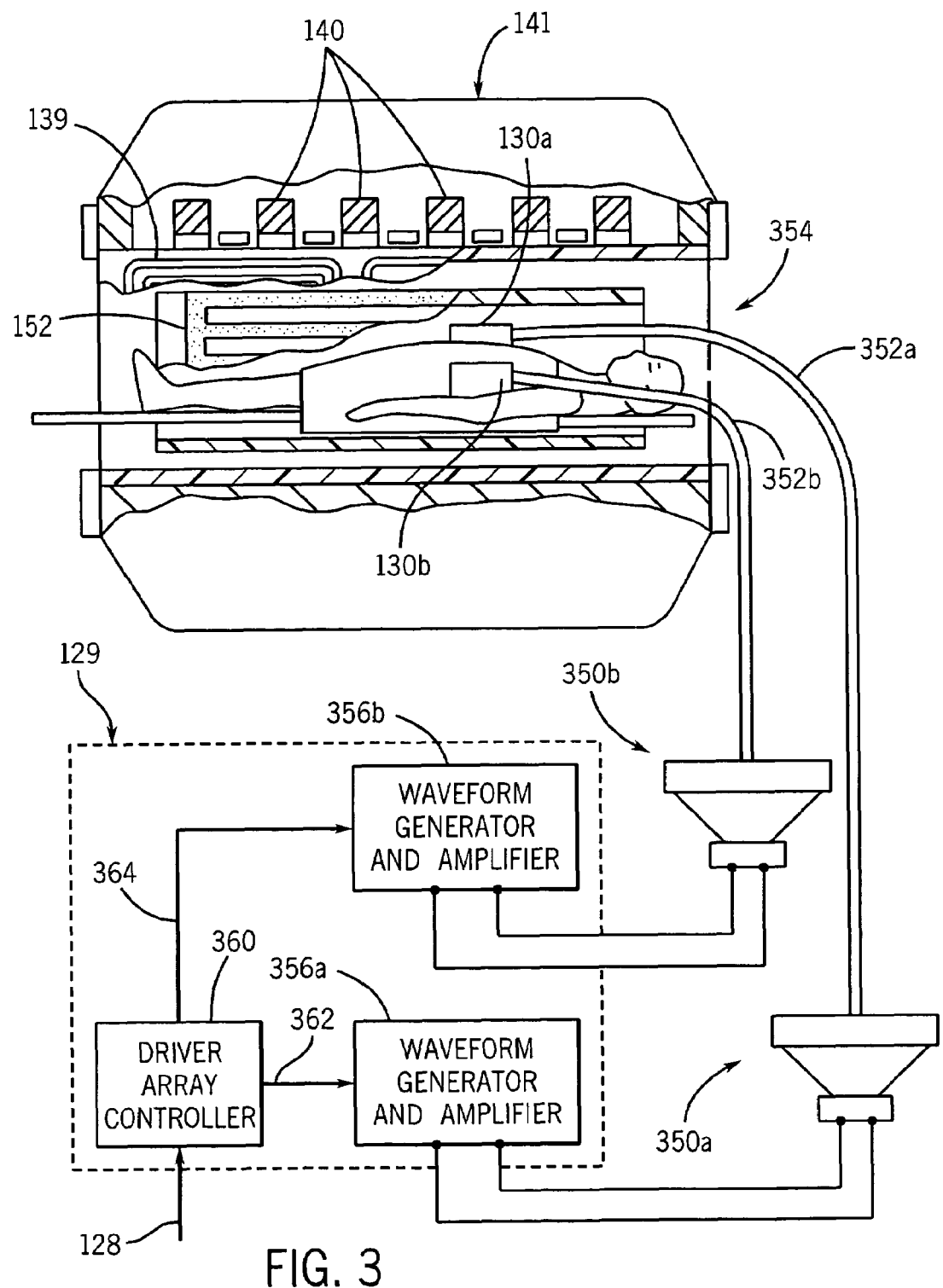
FIG. 3 is a block diagram of a portion of the MRI system of FIG. 1 showing an MRE driver array and wave generator and amplifier assembly.

Referring particularly to FIG. 3, in the preferred embodiment the transducer array 130 employs two pressure activated drivers 130a and 130b that are positioned at two locations on the subject of the examination. It should be apparent that additional drivers may be used and that different types of drivers may be used depending on the particular clinical application. As described in the above-cited co-pending U.S. patent application Ser. No. 10/860, 174, the drivers 130a and 130b are passive actuators that are connected to respective acoustic driver assemblies 350a and 350b by respective tubes 352a and 352b. The acoustic driver assemblies 350 are positioned away from the bore 354 of the magnet 141 and they each include a loudspeaker (not shown) that is electrically driven by respective waveform generator and amplifiers 356a and 356b to produce an acoustical pressure wave of the desired amplitude, frequency and phase. Their pressure waves are coupled through the tubes 352a and 352b to vibrate membranes (not shown) in the respective passive drivers 130a and 130b.

The waveform generator and amplifiers 356a and 356b form part of the assembly 129 that also includes a driver array controller 360. The driver array controller 360 receives "settings" from the pulse generator 121 in the MRI system through link 128, which indicate the frequency, amplitude and relative phase of the two drivers 130a and 130b during an MRE scan. These settings are employed to control the respective waveform generator and amplifiers 356a and 356b through links 363 and 364. The driver array controller 360 also receives the sync pulses 317 from the pulse generator 121 which indicate when the drivers 130 are to be operated during an MRE pulse sequence.

The settings which are downloaded to the driver assembly 130 prior to an MRE scan will depend on the particular clinical application and on the particular pixel is then calculated ($\phi=\tan^{-1}$ I/Q) as indicated at 383 to produce a phase image 375 which is indicative of the strain, or spin movement, in the tissue at each image pixel. To eliminate phase shifts caused by factors other than spin motion, one of two methods is typically employed. A reference phase image may be produced with the MRE data acquired when none of the drivers are active and this reference phase image is subtracted from each driver phase image. Preferably, however, a second set of driver phase images are acquired with the relative phase between the driver signals (as determined by sync pulses 317) and the alternating gradient 315 shifted 180 degrees. The driver phase images in the second, inverted set are subtracted from the corresponding driver phase images in the first set to remove undesired phase shifts.

As indicated above and shown in FIG. 5, several (e.g., eight) such strain images 375 are produced for each driver 130a and 130b, with the phase ($\psi$) between the driver signal and the motion encoding gradient 315 being different for each strain image 375. A strain wave peak amplitude image 377 and a strain wave phase image 378 is produced from these strain images 375 by calculating the Fourier Transform along the driver phase axis ($\psi$). The amplitude image 377 is calculated from the magnitude of the result at each image pixel and it indicates the peak strain amplitude at each pixel location in the ROI. The phase image 378 is calculated from the complex I and Q components of the result at each image pixel and it indicates the phase of the strain wave at each pixel location in the ROI. Together, the amplitude image 377 and the phase image 378 comprise the driver waveform response maps for one driver. This process is repeated for the data acquired from each driver in the array so that the magnitude and relative phases of the strain waves produced by each driver in the driver array is known.

Referring again to FIG. 4, the next step in the scan indicated by process block 376 is to optimize the strain waveform produced in the ROI when the separate strain waveforms produced by the drivers 130a and 130b are combined. In the preferred embodiment this is achieved by adjusting the phase of the drive signal to one driver such that the strain waves produced by both drivers 130a and 130b are in phase throughout the ROI. The amount of this phase adjustment is determined by examining the phase difference between ROI pixels in the strain wave phase images 378 for the two separate drivers 130a and 130b. More specifically, the phase adjustment is the average phase difference between corresponding pixels in the ROI of respective images 378. This phase adjustment is output as part of the settings downloaded to the driver array controller 360, as indicated by process block 390.

Referring still to FIG. 4, after the driver settings are downloaded, the MRE scan is performed as indicated at process block 382. As described in U.S. Pat. No. 5,592,085 the pulse sequence described in FIG. 2 is employed to acquire data for a number of images that are reconstructed as indicated at process block 382. During this acquisition the drivers 130a and 130b are both driven according to the downloaded settings and in response to sync pulses 317 produced by the pulse generator 121. Processing of the reconstructed image may also be performed to provide an indication of tissue stiffness as disclosed in U.S. Pat. No. 5,825,186 which is incorporated herein by reference.

While only two drivers 130a and 130b are employed in the transducer array described above, it is contemplated that the invention will be employed with transducer arrays having more drivers. The strain waves produced by each driver in an array can be measured separately and they can be separately controlled in amplitude and phase to produce the desired pattern of strain in the ROI when played together. When large numbers of transducers are used, for example, the phase and amplitude of their strain waves may be controlled to cancel one another in all but a very small volume of tissues that correspond to a suspected tumor. The suspect tumor tissues can thus be caused to oscillate during the MRE scan to provide information from which its stiffness and other mechanical characteristics may be determined.

The invention claimed is:

1. A method for producing a magnetic resonance elastogram (MRE) with a magnetic resonance imaging (MRI) system, the steps comprising:
    a) positioning a plurality of transducers on the subject to be imaged;
    b) energizing each transducer separately during a prescan;
    c) acquiring image data using an MRE pulse sequence while each transducer is separately energized and while the other transducers are unenergized;

d) reconstructing an image for each transducer using the image data acquired in step c);

e) determining optimal settings to drive each transducer using information derived from the reconstructed images; and f) acquiring an MRE image while the plurality of transducers are simultaneously energized using the optimal settings.

2. The method as recited in claim 1 in which the images reconstructed in step e) are strain images indicating the motion of spins in the subject produced by the respective transducers and step e) includes:

e)i) performing a complex Fourier transformation of the data acquired for each transducer to produce an image; and e)ii) producing a strain image from each image produced in step e)i) by calculating the phase at each image pixel.

3. The method as recited in claim 2 in which a plurality of strain images are reconstructed for each transducer and step e) further includes:

e)iii) producing a strain wave phase image for each transducer from the plurality of strain images.

4. The method as recited in claim 3 in which step e)iii) includes performing a Fourier transformation on the plurality of strain images.

5. The method as recited in claim 3 in which one of the settings is the phase of the signal used to drive the transducer and the phase setting is derived from the strain wave phase image.

6. The method as recited in claim 3 in which image data acquired in step d) is acquired while the transducer is driven at a plurality of different phases, and the plurality of strain images correspond to the plurality of different phases.

7. A transducer array for use in performing a magnetic resonance elastography scan, the combination comprising:

a plurality of transducers for positioning on the subject to be imaged and each transducer being operable in response to a drive signal to apply an oscillating force to the subject; and a driver array controller for controlling the frequency and relative phase of the drive signal applied to each transducer in accordance with settings produced during a prescan procedure, the driver array controller being operable during the magnetic resonance elastography scan to simultaneously drive the plurality of transducers.

8. The transducer array as recited in claim 7 which includes a waveform generator and amplifier connected to each of said plurality of transducers for producing the drive signals, and the driver array controller is connected to control each of said waveform generators and amplifiers in accordance with the settings.

* * * * *

UNITED STATES PATENT AND TRADEMARK OFFICE
CERTIFICATE OF CORRECTION

PATENT NO. : 7,307,423 B2  Page 1 of 1
APPLICATION NO. : 11/122424
DATED : December 11, 2007
INVENTOR(S) : Ehman et al.

It is certified that error appears in the above-identified patent and that said Letters Patent is hereby corrected as shown below:

Title Page

Item (73) Assignee, "Wisconsin A.umni Research Foundation, Madison, Wisconsin" should read --Mayo Foundation For Medical Education and Research, Rochester, Minnesota--.

Signed and Sealed this

Seventh Day of October, 2008

JON W. DUDAS
*Director of the United States Patent and Trademark Office*